United States Patent [19]
Rolf

[11] Patent Number: 4,674,512
[45] Date of Patent: Jun. 23, 1987

[54] MEDICAL ELECTRODE FOR MONITORING AND DIAGNOSTIC USE

[75] Inventor: David Rolf, Minneapolis, Minn.

[73] Assignee: LecTec Corporation, Minnetonka, Minn.

[21] Appl. No.: 825,751

[22] Filed: Feb. 3, 1986

[51] Int. Cl.$^4$ ............................................. A61B 5/04
[52] U.S. Cl. ................................................... 128/640
[58] Field of Search .............................. 128/639–641, 128/798, 802, 803

[56] References Cited

U.S. PATENT DOCUMENTS

| | | | |
|---|---|---|---|
| 4,016,869 | 4/1977 | Reichenberger | 128/640 |
| 4,273,135 | 6/1981 | Larimore et al. | 128/640 |
| 4,274,420 | 6/1981 | Hymer | 128/641 |
| 4,554,924 | 11/1985 | Engel | 128/640 |

Primary Examiner—Lee S. Cohen
Attorney, Agent, or Firm—James V. Harmon

[57] ABSTRACT

A medical electrode is provided which includes a flexible tin backing coated with a flexible hydrated gel matrix adapted to contact and conform to the skin. The matrix is composed of a hydrated polysaccharide gum, a liquid hydrating agent such as a polyhydric alcohol and water, an electrolyte including one or more tin salts dissolved in the liquid and preferably a stabilizer present in sufficient quantity to prevent the tin salts from forming insoluble reaction products.

10 Claims, 3 Drawing Figures

MEDICAL ELECTRODE FOR MONITORING AND DIAGNOSTIC USE

FIELD OF THE INVENTION

The present invention related to medical electrodes and more particularly to an improved flexible electrode that is attached to the skin for monitoring and diagnostic use.

BACKGROUND OF THE INVENTION

U.S. Pat. Nos. 4,274,420 and Re. 31,454 describe flexible medical electrodes composed of a flexible silver foil backing to which is applied a flexible substrate or matrix containing a hydrophilic hydrocolloid, a hydrating liquid e.g. glycerin and an electrolyte to render the flexible hydrated gel electrically conductive. It has also been proposed for example in U.S. Pat. Nos. 4,419,998 and 4,494,552 to provide a combination heart monitoring and defibrillation electrode for medical use that includes a metal backing composed of tin having a layer of stannous chloride sprayed onto one surface. Over the stannous chloride layer is applied a porous foam disc adapted to receive an electrically conductive medium such as a saline gel. These electrodes while generally effective have certain disadvantages. The need for a laminate of several layers of material increases production costs. Moreover, soluble substances can diffuse from one layer to another allowing chemical changes to take place during shipment, storage and use. In addition, the foam material adds to the weight and bulk of the electrode but does not assist in carrying electric current. Moreover, delamination is possible between layers which may under some circumstances interfere with the conduction of current from one layer to another. At the present time, most medical electrodes used for monitoring purposes which require application over extended periods of time include a conductive silver/silver chloride material connecting the conductive gel to the metal snap. Electrodes having tin foil backing have been used successfully in a large commercial scale only for diagnostic purposes which generally require application for only a few minutes time. One of the major objectives of the present invention is to find a way to construct an effective, commercially functional medical electrode with a tin foil backing coated with a hydrophilic matrix containing a hydrocolloid in a hydrated state that can be used both for diagnostic as well as for monitoring use over a time period of many hours and which during use will have performance characteristics not unlike the more expensive electrodes containing silver/silver chloride conductive material.

In the development work leading to the present invention, electrodes were prepared using a tin foil backing coated with a hydrophilic gel containing a tin salt such as tin chloride dissolved in the gel. Such electrodes while they were effective for some purposes did not have good shelf life for some applications. Moreover, premix solutions used in the manufacture of these gels, containing tin salts, were unstable and heterogeneous.

To understand the requirements of the present electrode, some of the problems of clinical use will be briefly reviewed. One of the desired objectives is to provide a non-silver/silver chloride containing electrode which can be used for monitoring applications. However, to be effective such an electrode must depolarize quickly after a defibrillation stimulus of approximately 200 volts is discontinued. A diagnostic electrode that remains polarized following defibrillation is ineffective in picking up EKG signals from the heart. Depolarization is particularly important since following defibrillation with an ineffective electrode, the heart monitor trace will flip out of view on the screen and will not come back because the electrode itself looks like a battery to the monitor. Thus the monitor can not be used to tell if a patient is recovering following defibrillation.

A major goal is to provide effective coupling at the interface between the electrically conductive gel and the metal foil layer. This will permit rapid depolarization of the electrode after defibrillation. If the coupling is satisfactory, the electrode will exhibit a relatively low and constant D.C. offset, i.e. one that is constant over time rather than rising over a period of time after it is applied to the skin. D.C. offset is a minute current produced by the electrochemical makeup of the electrode itself. To be satisfactory the electrode should have a D.C. offset no greater than about 100 millivolts.

In addition, to be satisfactory a high performance electrode should have relatively low impedance at low frequencies, especially for EEG applications. For example, if a tin foil backing is coated with a hydrated flexible hydrophilic gel matrix containing sodium chloride as an electrolyte, the impedance will rise rapidly when the electrode is subjected to an applied alternating current as the frequency of that current decreases (say 100 to 10 cycles cycles per second). By contrast, commercially acceptable silver/silver chloride electrodes exhibit an impedance which is substantially constant when subjected to an AC current over the same range of frequencies. An electrode will not exhibit the desired uniform impedance characteristics if its hydrophilic gel composition is incompatible or does not couple well to the metal foil backing.

The desired electrode should exhibit two effects; first, rapid depolarization of charged internal layers caused by defibrillation pulses and second, relatively low and constant DC offset as well as constant impedance with a fluctuating voltage applied at various frequencies. Low impedance is important because it will provide a lower noise to signal ratio.

SUMMARY OF THE INVENTION

Briefly, the present invention provides a medical electrode device for establishing electrical contact with the skin which includes a flexible electrically conductive backing layer composed of tin coated on its lower surface with an electrically conductive flexible substrate of a novel composition. The substrate or matrix coated on the lower surface of the tin layer is preferably homogenous. It is hydrophilic and sufficiently pliant to conform to the shape of the body contours when attached to the skin. The matrix includes a dispersed phase comprising about 10 percent to 50 percent of the total of the matrix formed from a hydrophilic natural or synthetic polysaccharide gum or a hydrophilic synthetic polymer or both and a liquid phase hydrating the matrix and converting the matrix to a hydrocolloidal suspension. The liquid phase includes a polyhydric alcohol and a dissolved electrolyte to render the matrix electrically conductive including at least one tin salt such as $SnSO_4$, $SnCl_2$, $SnBr_2$, $SnCl_2.2H_2O$ and $SnF_2$, or the tin salt of an organic acid such as a multibasic organic acid including tin tartrate and tin citrate among others. The matrix is self supporting i.e. it retains its shape without assistance.

A stabilizer is preferably provided to prevent the tin salt from reacting with other chemical constituents of the matrix. While various stabilizing agents can be used, among the preferred stabilizing agents is tartaric acid and its alkali metal salts, polyacrylic acid and its alkali metal salts or other neutralized forms thereof, n-alkyl sulfonates wherein n comprises 8 to 16 carbon atoms, citric acid and its alkali metal salts, soluble nitrate salts particularly the alkali metal salts thereof and ascorbic acid and its basic salts. The stabilizing agent is preferably present in an amount at least great enough to maintain tin ions in solution within the matrix at room temperature (15°–25° C.). These stabilizers prevent undesired tin reaction products. It was found that the tin salts dissolved in water premix solutions only initially. In a short while, precipitates form due to hydrolysis. These precipitates are amorphous tin oxides and hydroxides. This instability also lowers the pH of water premixes interfering with efficient manufacturing and consistently reliable end product. However, the stabilizers virtually eliminate these reaction products and make it possible to achieve the desired results with less of the tin salt present. This is desirable since less corrosion of the tin layer will occur, skin sensitivity will be reduced and the pH of the composition will tend to remain closer to neutral.

The invention will be described by way of example in connection with the accompanying drawings wherein.

DESCRIPTION OF THE PREFERRED EMBODIMENTS

Medical electrodes are used in large numbers in increasing applications such as monitoring impulses from the heart or brain. While a variety of medical electrodes of different forms and physical construction can be used in connection with the present invention, the invention will be described by way of example using two forms of snapless or tab type electrodes. It should be understood, however, that the invention can be employed with a variety of electrodes of different physical forms including those with snaps.

Figure 1:
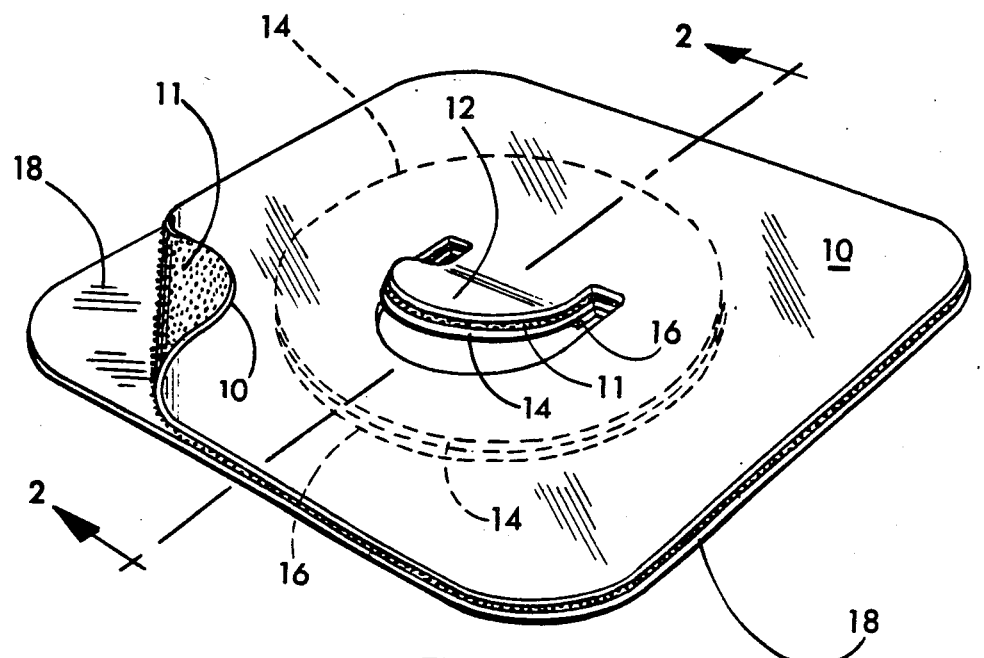
FIG. 1 is a perspective view of one form of electrode embodying the invention.

FIG. 1 is a top perspective view which shows the non-adhering surface of a generally rectangular section of pressure sensitive tape 10 that has been die cut with a U-shaped cut in the central portion to provide a U-shaped tab 12 at the center.

Figure 2:
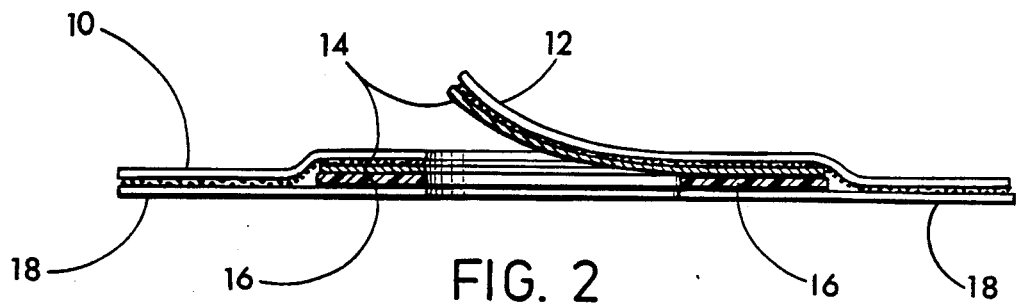
FIG. 2 is a perspective view of another form of electrode embodying the invention.

The cross sectional view of FIG. 2 shows the relative positioning of the pressure sensitive tape layer 10 and a conductive layer 14 which comprises for example, a metal or metal alloy composed of tin, a uniformly conductive flexible substrate or matrix 16 and a removeable protective liner 18. The matrix 16 is a flexible hydrated hydrophilic gel which is sufficiently pliant to conform to the shape of the body contours. The composition of the matrix will be more fully described below.

The pressure sensitive tape layer 10 is coextensive with a removeable protective liner 18 and a flexible substrate or matrix 16 is coextensive with the uniformly conductive flexible tin layer 14. The tin layer 14 and the matrix 16 are positioned concentrically within the larger pressure sensitive tape 10 such that the tape extends beyond the edge of the metallic layer 14 to provide a periphally extending downwardly facing exposed pressure sensitive surface 11 to adhere to the skin. The pressure sensitive surface 11 at least partially surrounds the layers 14 and 16 or may extend along two parallel strips on either side thereof. In other embodyments these layers may take a variety of shapes which provide a centrally located tab used to easily establish electrical contact on at least one side of the tin layer 14. Electrical contact with both sides of the metallic layer 14 is accomplished by cutting out the tab 12 portion of the tape. A generally U-shaped cut through the tape 10 on layers 14 and 16 will thus define the tab 12. It will be noticed that the tab 12 provides a hole through which the skin may be seen thereby providing an area of breathability in the center of the electrode.

The substrate or matrix 16 is composed of a uniformly electrically conductive flexible hydrated hydrocolloidal mass capable of establishing electrical contact with the skin. It may or may not have adhesive properties.

Figure 3:
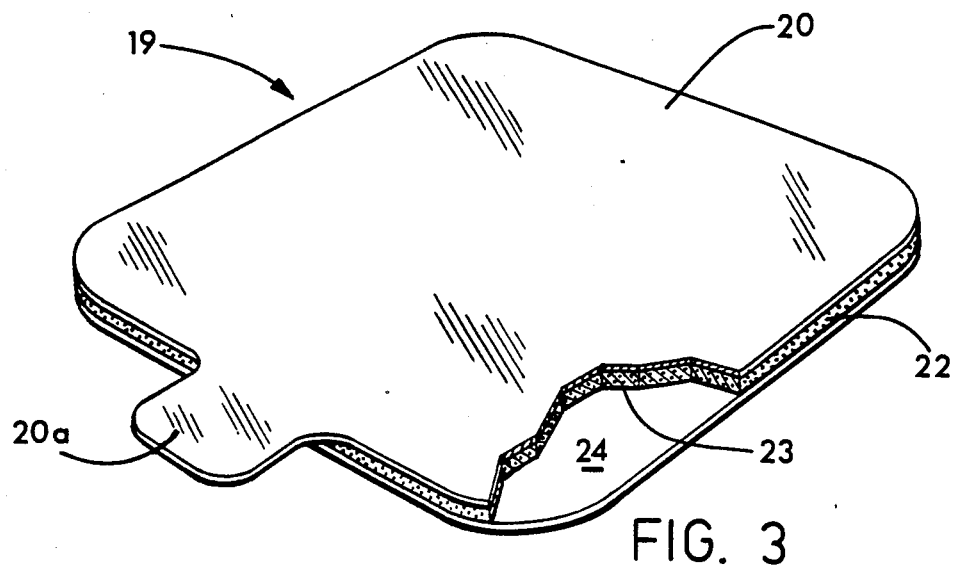
FIG. 3 is a perspective view of another form of electrode embodying the invention.

Refer now to FIG. 3 which illustrates another embodiment of the invention. In this case an electrode 19 is composed of electrically conductive layer of tin 20 in the form of flexible foil that may if desired be provided with strong plastic backing (not shown). The metallic layer 20 is provided with a laterally extending tab 20a which projects outwardly from one edge thereof for the attachment of electrical contacts when the electrode is to be used. At least one of the surfaces of the tab 20a should be exposed so that good electrical contact can be made. Bonded to the lower surface of the tin foil layer 20 is a matrix 22 having a tacky or gummy lower surface 23, the adhesive properties of which hold the electrode in contact with the skin. Releasably bonded to the lower surface 23 of the matrix 22 is a removable cover or liner layer which is withdrawn and discarded just before the electrode 19 is to be used. Because of its gummy or tacky lower surface 23 the matrix 22 can be thought of as a self-adhering or self-bonding matrix which adheres to the skin both through its tackiness and also through its ability to conform to the body contours and to become mechanically bonded to skin irregularities and even to extend into openings such as pores, interstices between cells and the like.

The matrix 16 or 23 as the case may be, attached to the conductive layer is substantially homogeneous. It is composed of a hydrated hydrophilic stable matrix that is sufficiently pliant to conform to the shape of the body contours. The matrix includes a dispersed phase of about 1%–50% of the total weight of the matrix formed from a hydrophilic natural or synthetic gum and/or a hydrophilic synthetic polymer. A liquid phase includes a polyhydric alcohol such as glycerin or propylene glycol or a mixture thereof. An electrolyte of any suitable salt which is non-toxic under the conditions of use is provided to render the matrix electrically conductive. The electrolyte includes at least one tin salt to be described more fully below and a stabilizer in sufficient quantity to prevent the precipitation of tin reaction products.

Of the naturally occurring gums that may be used are gum Karaya, gum acacia, locust bean gum and other polysaccharide gums and synthetically formulated gums such as modified guar gums and celluloses such as carboxymethyl cellulose, hydroxypropyl cellulose and the like. The matrix may also include synthetic polymers such as polyacrylamide, polyacrylic acid and a modified starch such as pregelatinized starch. The synthetic polymers and/or synthetic or natural gum and other polysaccharides constitute the solid hydrated dispersed phase of the matrix.

The liquid phase of the matrix preferably comprises the aforementioned polyhydric alcohol and water. Other hydrating and solublizing agents or humectants will be apparent to those skilled in the arts. The solid portion of the matrix can comprise about 10% to about 50% of the matrix. The liquid phase composed of polyhydric alcohol and/or water comprises the balance namely 50 to 90% of the matrix. The hydrophilic gum or hydrophilic polymer mixture thereof may be present in the amount of between 10% to 50% by weight of the matrix. All quantities and percentages stated herein are expressed as a weight percent of the total matrix. The polyhydric alcohol may be present in an amount of between 10% to 65% of the matrix and the water may be present in an amount of about 1.0% to 25% by weight. The electrolytic salt should be present in an amount sufficient to render the matrix electrically conductive. Typically, the amount of salt present is from about 1% to about 8%. The stabilizer when used is present in the amount of from about 0.1% to about 2% by weight.

The finished matrix is a somewhat elastic flexible hydrophilic layer that may be typically from about 1/32 to about ⅛ of an inch in thickness. When applied to the skin, body moisture as well as body salts and heat are absorbed increasing its tackiness and causing the surface materials to soften and to tend to go into solution. As a result the matrix of the embodiment shown in FIG. 3 will flow into the pores and other irregularities in the skin creating a mechanical interlock bond with the skin in addition to the already present adhesive bond. The bonding and elastic properties of the electrode are enhanced as it ages in contact with the skin.

Several tin salts can be used. Among them are tin halides such as $SnF_2$, $SnBR_2$, $SnCl_2$ and $SnCl_2.2H_2O$. Compounds of tin with sulfur such as $SnSO_4$ and organic acids including tin tartrate and tin citrate. It was found that the tin salts alone were unstable in the matrix and aqueous premixes used in manufacture. For example, a solution of $SnSO_4$ in water after 24 hours contains 32% insolubles which increases to about 35% in another 24 hours. If the solution is agitated the percentage of insolubles increases to 77% after 72 hours. While $SnCl_2$ is more soluble, about 16% precipitates after 48 hours and about 19% is insoluble after 72 hours. The insolubles are believed to be primarily hydrated tin oxides and hydroxides. This is, of course, undesirable since it removes active tin ions from solution making them unavailable for electrical conduction. The formation of undesirable tin reaction products is prevented by the addition of a stabilizer in sufficient quantities to maintain the tin ions in solution at room temperature (15° C.–25° C.).

Among the stabilizers that have been found suitable are tartaric acid and its alkali metal salts, polyacrylic acid and its sodium salts or other neutralized forms thereof, n-alkyl sulfonates wherein n is from 8 to 16 carbon atoms, citric acid and its alkali metal salts, soluble nitrate salts such as the alkali metal salts thereof and ascorbic acid and its basic salts. Stabilizers help to keep metal salts and particularly tin salts in solution by preventing undesired reaction products. Accordingly, they prevent deterioration during shipment and storage and assure that the electrical characteristics will be maintained. The stabilizers, when present, are used in an amount of 0.1% to 2%.

The polyhydric alcohol should be present in an amount between 10 to 65%. Its effect is to swell the hydrophilic polymer and help to dissolve some of the electrolytes. It is also involved in hydrogen bonding and cross linking. Too much tends to make the product mushy, runny, soft or greasy feeling, and too little causes the product to be hard and dry usually less tacky. Propylene glycol is a less effective hydrating substance than glycerin.

Water is preferred in an amount from about 1 to 25% by weight of the matrix primarily for the purpose of swelling the hydrophilic polymers thus building viscosity and for helping to dissolve the salts to enhance their conductivity. Too much water will make the products soft, weak or over swollen and will tend to interfere with efficient processing during the manufacturing process. If too little water is used, the matrix may lack electrical conductivity, salts may not dissolve and the product may tend to be hard and dry.

The amount of hydrophilic polysaccharide gum used can be varied from about 10 to 50% by weight. The hydrophilic polysaccharide gums build viscosity by hydrogen bonding eventually becoming semi-solid. Excessive amounts cause the formula to become too thick and viscous to be coated evenly and the product tends to be lumpy. However, if too little is used the product may be soft, mushy or runny. The gum also acts as a humectant.

The hydrophilic synthetic polymers when present are preferably used in an amount from about 5 to 25% of the composition to add strength and/or tackiness. One example is anionic polyacrylamide, a copolymer of acrylamide and acrylic acid. This material is sold as Reten 521PX by Hercules Chemical Company of Willmington, Del. If used in excess the viscosity of the formula becomes excessive, unworkable and lumpy. If too little is used the matrix may be soft or runny.

One suitable emulsion adhesive polymer is a copolymer of di-octylmaleate and vinyl acetate as an emulsion containing about 50% water. This product is sold under the name Flexbond One Fifty by the Air Products Company of Allentown, Pa. These polymers if present in excess reduce pot life and cause material to become too tacky. However, if too little is used, tack may be insufficient and the product may not adhere well to the tin foil backing.

Polyacrylic acid having a molecular weight of about 50,000 is available from Poly Sciences, Inc., Warrington, Pa. It assists in building viscosity by hydrogen bonding. Its low pH can be increased by adding caustic which will enhance its thickening properties. It is used in amount of about 1 to 20% as a thickener and tackifier. It also helps in stabilizing the formulation. If too much is used, the matrix is too viscous and unworkable or lumpy. If too little is used, the composition becomes soft or runny.

Among the salt that can be used to assist in electrical conductivity other than those already mentioned, are sodium chloride, sodium nitrate and potassium choride. Enough should be used to render the composition a good conductor of electricity. Sodium chloride is used, for example, in amount of from about 1 to 6% along with other salts to provide a total salt content of 7 or 8%. If too little is used the electrode will have insufficient conductivity. If too much is used, insoluble salt particles may be present in the composition.

The tin salts already mentioned cooperate with other salts in the formulation to improve conductivity. It was also found that they assist in recovery of the electrode i.e. depolarization following defebrillation by establishing an efficient electrical coupling at the gel-metal interface. The tin salts are usually used in an amount of from 0.1% to about 1%. If too much is used, it may be insufficiently dissolved causing cloudiness and possible skin irritation. If too little is used it may not be possible to achieve the above described performance characteristics.

The following procedure is used in compounding, extruding and curing the electrodes. It is preferred to use a premix to combine soluble salts and polar liquids such as water and glycerin. The least polar solution is first combined with the hydrophilic polymers. Progressively more polar solutions are added and mixing is continued until homogeneous. Care is taken to prevent aeration of the formula during the addition. Mixing is carried out in a pitched propellar blade agitator until homogeneous. Since the viscosity is increasing after and during mixing, it is preferred to mix the composition continuously rather than by the batch at a rate which material for extrusion through an orifice onto the backing material and for later curing. Curing is accomplished by allowing the product to remain in storage for a period of time but can be hastened by infrared radiation or other source of heat. Heating increases the rate of bond rearrangement to form a continuous network of hydrogen bonds throughout the gel.

The electrodes of the present invention provide a quick recovery following defibrillation and a relatively low level and constant impedance throughout a range of applied alternating current frequencies and exhibit DC offset stability at least equal to prior electrodes containing silver/silver chloride but have a substantially reduced cost. Moreover, since a single layer of homogeneous matrix material 16 is used production costs are no higher than the least expensive of this kind.

The invention will be better understood by reference to the following examples:

EXAMPLE 1

| | OPTIMUM WT. RANGE AS A PERCENT OF THE MATRIX | TYPICAL |
|---|---|---|
| Karaya Gum | 20–40% | 29.3% |
| Vinyl acetate based latex adhesive (Flexbond 150, Air Products Inc., Alantown PA) | 1–10% | 2% |
| Water | 1–10% | 8% |
| Glycerin | 40–60% | 57% |
| NaCl | 2–5% | 3% |
| $SnCl_2.2H_2O$ | .2–1% | 0.2% |
| Sodium Tartarate Stabilizer | .2–2% | .5% |
| | | 100.0% |

EXAMPLE 2

| | OPTIMUM WT. RANGE AS A PERCENT OF THE MATRIX | TYPICAL |
|---|---|---|
| Karaya gum | 20–40% | 30% |
| Glycerin | 40–60% | 56.3% |
| Water | 1–10% | 9% |
| NaCl | 2–5% | 4% |
| $SnSO_4$ | .2–1% | .2% |
| n-alkyl sulfonate stabilizer | .2–2 | .5% |
| | | 100.0% |

EXAMPLE 3

| | OPTIMUM WT. RANGE AS A PERCENT OF THE MATRIX | TYPICAL |
|---|---|---|
| Karaya gum | 10–20% | 15% |
| Anionic polyacrylamide | 5–20% | 12.3% |
| Flex bond 150 | 5–20% | 9% |
| Water | 2–15% | 6% |
| NaCl | 2–8% | 2% |
| Glycerin | 50–60% | 55.0% |
| $SnSO_4$ | 0.1–1% | .2% |
| K citrate stabilizer | .5–2% | .5% |
| | | 100.0% |

EXAMPLE 4

| | OPTIMUM WT. RANGE AS A PERCENT OF THE MATRIX | TYPICAL |
|---|---|---|
| Karaya gum | 10–50% | 30% |
| Propylene glycol | 10–50% | 45% |
| Water | 10–25% | 20% |
| NaCl | 2–6% | 4% |
| $SnBr_2$ | 0.1–1% | .1% |
| Sodium nitrate stabilizer | .2–2% | .9% |
| | | 100.0% |

EXAMPLE 5

| | OPTIMUM WT. RANGE AS A PERCENT OF THE MATRIX | TYPICAL |
|---|---|---|
| Anionic polyacrylamide | 10–25% | 15% |
| Vinyl acetate based latex additive (Flexbond 150) | 2–10% | 8.8% |
| Glycerine | 45–65% | 55% |
| Water | 7–20% | 14.5% |
| $NaNO_3$ | 1–5% | 4% |
| Stabilizer and electrolyte | | |
| $Mg(OAc)_2$ | 1–4% | 2% |
| $SnF_2$ | .1–1% | .2% |
| NaCl | 0–6% | .5% |
| | | 100.0% |

EXAMPLE 6

| | OPTIMUM WT. RANGE AS A PERCENT OF THE MATRIX | TYPICAL |
|---|---|---|
| Karaya gum | 10–35% | 30% |
| Polyacrylic acid | 1–20% | 5% |
| Polyacralamide | 2–10% | 5% |
| NaCl | 1–4% | 3% |
| Glycerine | 40–50% | 50% |
| $SnCl_2.2H_2O$ | .1–1% | .2% |
| Water | 1–10% | 6.8% |
| | | 100.0% |

EXAMPLES 7-11

Matrices are prepared as in Example 4 except that in each successive example sodium nitrate is replaced by an equal weight of the following stabilizers: Example 7—tartaric acid, Example 8—sodium polyacrylate, Example 9—citric acid, Example 10—ascorbic acid and Example 11—sodium ascorbate.

EXAMPLES 12 & 13

Matrices are prepared as in Example 1 except that the sodium tartrate is replaced with the following: Example 12—tin tartrate 0.2% by weight. Example 13 tin citrate 0.2% by weight.

What is claimed is:

1. An electrode device for establishing electrical contact with the skin comprising, a flexible electrically conductive metallic layer comprising tin, and electrically conductive flexible substrate attached to said conductive layer comprising a substantially homogeneous, hydrated hydrophilic, stable self supporting matrix sufficiently pliant to conform to the shape of the body contours, said matrix including a dispersed phase comprising about 10 percent to 50 percent of the total weight of the matrix and formed from a hydrophilic natural and/or synthetic polysaccharide gum and/or a hydrophilic synthetic polymer and a liquid phase hydrating the matrix and converting the matrix to a hydrocolloidal suspension, said liquid phase comprising at least one polyhydric alcohol, an electrolyte to render the matrix electrically conductive comprising at least one dissolved tin salt comprising a member selected from the group consisting of $SnSO_4$, $SnCl_2$, $SnCl_2.2H_2O$ and $SnF_2$ and a thin salt of $SnBr_2$, a multibasic organic acid distributed throughout the matrix and being present at an exposed surface of the matrix adapted to contact the skin, a stabilizer in sufficient quantity to maintain the tin ions in solution at room temperature thereby preventing the formation of insoluble tin salts, said stabilizer comprising a member selected from the group consisting of tartaric acid, n-alkyl sulfonate wherein n is from 8–16 carbon atoms, citric acid and an alkali metal salt of citric acid, whereby said stabilizer mainstains the pH of the composition, reduces corrosion of the tin layer and lessens skin sensitivity reactions.

2. The electrode of claim 1 wherein the gum comprises karaya gum.

3. The electrode of claim 2 wherein the karaya gum is present in an amount of from about 10–50% by the weight of the matrix.

4. The electrode of claim 1 wherein the hydrophilic synthetic polymer comprises anionic polyacrylamide in an amount of from about 2 to about 20% by weight of the matrix.

5. The electrode of claim 1 wherein the hydrophilic synthetic polymer comprises vinyl acetate based latex adhesive.

6. The electrode of claim 1 wherein the synthetic polymer is polyacrylic acid in the amount of from about 1 to about 20% of weight of the matrix.

7. The electrode device of claim 1 wherein the tin salt comprises $SnSO_4$ in the amount of about 0.1% to 1% by weight of the matrix.

8. The electrode device of claim 1 wherein the tin salt is $SnCl_2$ in the amount of about 0.1% to 1% by weight of the matrix.

9. The electrode device of claim 1 wherein the tin salt is $SnF_2$ in the amount of about 0.1% to 1% by weight of the matrix.

10. The electrode of claim 1 wherein the tin salt is $SnCl_2.2H_2O$ in the amount of from about 0.1% to 1% by weight of the matrix.

* * * * *

UNITED STATES PATENT AND TRADEMARK OFFICE
CERTIFICATE OF CORRECTION

PATENT NO. : 4,674,512
DATED : June 23, 1987
INVENTOR(S) : David Rolf

It is certified that error appears in the above-identified patent and that said Letters Patent is hereby corrected as shown below:

Column 3, delete lines 33 and 34 and insert

-- Fig. 2 is a cross-sectional view taken on line 2-2 of Figure 1. --

Claim 1, line 3, "and" should read -- an --

Line 25, before "$SnSO_4$" insert -- $SnBr_2$,--

Line 26, cancel "$SnBr_2$,".

Signed and Sealed this

Second Day of February, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,674,512
DATED : June 23, 1987
INVENTOR(S) : David Rolf

It is certified that error appears in the above-identified patent and that said Letters Patent is hereby corrected as shown below:

Column 9, line 26, "thin" should read -- tin --.

Signed and Sealed this

Twenty-eighth Day of June, 1988

Attest:

*Attesting Officer*

DONALD J. QUIGG

*Commissioner of Patents and Trademarks*